United States Patent [19]

Bochis

[11] 4,092,321
[45] May 30, 1978

[54] PROCESS FOR THE PREPARATION OF IMIDAZO [1,2-a] PYRIDINES

[75] Inventor: Richard J. Bochis, East Brunswick, N.J.

[73] Assignee: Merck & Co., Inc., Rahway, N.J.

[21] Appl. No.: 806,974

[22] Filed: Jun. 16, 1977

[51] Int. Cl.$^2$ ............................................. C07D 471/04
[52] U.S. Cl. ............................... 260/294.8 C; 424/256
[58] Field of Search ................................ 260/294.8 C

[56] References Cited

U.S. PATENT DOCUMENTS 3,701,780   10/1972   Fisher ............................ 260/294.8 C

OTHER PUBLICATIONS

Fisher et al., Jr. of Medicinal Chem. vol. 15, pp. 982–985 (1972).
Krohrke et al., Chem. Ber., vol. 88, pp. 1117–1121, (1955).

*Primary Examiner*—John M. Ford
*Attorney, Agent, or Firm*—David L. Rose

[57] ABSTRACT

Processes are described for the preparation of 2-(methoxycarbonylamino)-6-(phenylsulfinyl) imidazo [1,2-a] pyridine, which is an active anthelmintic agent. The process involves the treatment of a 5-phenylsulfinyl pyridine substituted at the 2-position with a leaving group, with methylchloroacetylcarbamate followed by treatment with ammonia.

6 Claims, No Drawings

PROCESS FOR THE PREPARATION OF IMIDAZO [1,2-a] PYRIDINES

SUMMARY OF THE INVENTION

This invention is concerned with processes for the preparation of 2-(methoxycarbonylamino)-6-(phenylsulfinyl) imidazo [1,2-a] pyridine, which is an active anthelmintic agent. The process involves the treatment of a 5-phenylsulfinyl pyridine which is substituted at the 2-position with a leaving group such as a halogen, a loweralkoxy or a loweralkylthio group, with methylchloroacetylcarbamate. The quaternary intermediate thus formed is treated with ammonia, preferably in the presence of a protic solvent in order to form the desired product. Thus it is an object of the present invention to described such processes for the preparation of the indicated compound. A further object of this invention is to describe the preparation of the starting materials employed in these processes. Still further objects will become apparent upon reading the following description.

The compound 2-(methoxycarbonylamino)-6-(phenylsulfinyl) imidazo [1,2-a] pyridine is depicted structurally as:

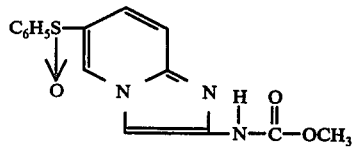

and the imidazo [1,2-a] pyridines nucleus is numbered as follows:

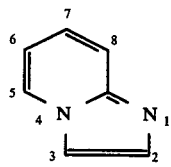

The process of this invention is depicted schematically in the following reaction:

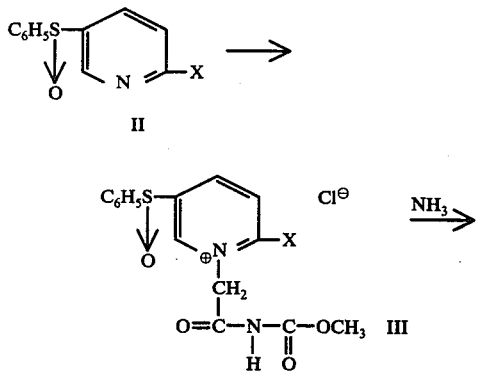

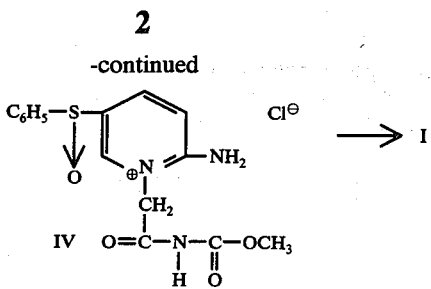

wherein X is a leaving group selected from a halogen, such as chlorine, bromine or iodine; loweralkoxy or loweralkylthio. The preferred leaving groups are chlorine, bromine, methoxy and methylthio.

The position of the positive charge in structure IV may not be precisely assignable, but rather the structure as above written may be in equilibrium with the following:

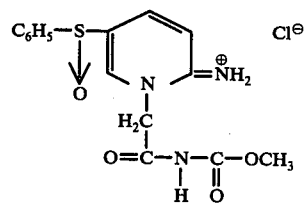

In the foregoing reaction scheme the 5-phenylsulfinyl pyridine substituted at the 2-position with the X leaving group (II) is treated with methylchloroacetylcarbamate. The reactants are generally combined in a solvent which for optimum results should be a polar aprotic solvent. Suitable solvents are acetonitrile, dimethylformamide, hexamethylphosphoramide, dimethylacetamide, dimethoxyethane, triethylphosphate and the like. The reaction is carried out at from 50° to 150° C over a period of from 1 to 50 hours, however, it is preferred to heat the reaction at from 75° to 100° C for 1 to 24 hours. The reaction product is a quaternary ammonium salt and remains in solution at the conclusion of the reaction. By diluting the reaction mixture with large amounts of ether, it would be possible to isolate compound III. However, generally it is preferred not to isolate the product.

Compound III is then treated with an excess amount of ammonia which displaces the leaving group X and forms the 2-amino compound. The reaction is run at rom temperature or less, preferably from 0° C to room temperature. The reaction mixture is stirred at the above designated temperatures for from 5 minutes to 2 hours.

The 2-amino compound is not necessarily isolated. It is preferred to cyclize the 2-amino compound in situ by heating the reaction mixture at temperatures up to 100° C for from 1 to 4 hours. It has been found that the reaction is facilitated by the addition of a protolytic source to the reaction mixture prior to heating. Methanol is preferred especially in quantities in excess of a single molar equivalent. A variation of the above would entail the addition of a quantity of ammonia saturated methanol to the solution of compound III, and completing the reaction as described. Following the above described heating step, the product (I) is isolated using known techniques.

The starting materials for the above process are prepared by different procedures, depending upon the nature of the X substituent.

When X is halogen compound II is prepared from 5-phenylthio-2-amino pyridine by diazotization in the presence of halogen ions. The reaction is carried out in aqueous mineral acid, preferably a hydrohalic acid wherein the halogen of the acid matches the halogen atom to be added onto the substrate. The starting 2-amino starting material is combined with the mineral acid and an equimolar quantity of sodium nitrite is slowly added. The addition must be of such a rate that the temperature does not exceed 10° C. When the addition is complete, the reaction mixture is allowed to rise to about 15° C and the solution neutralized with a strong base such as sodium or potassium hydroxide maintaining the temperature at 15° C or less. When the solution is neutral, it is extracted with an organic solvent to isolate the product 2-halo-compound (II, X=halogen).

The 2-chloro compound may also be prepared from phosphorous pentachloride in phosphorous oxychloride. The reaction mixture is heated to 100° C for from 1-6 hours and the phosphorous oxychloride removed, and the residue added to ice. The chloro compound is then isolated using known techniques.

The compound where X is loweralkoxy, preferably methoxy, is prepared from the 2-chloro or bromo compound and sodium methoxide. The reaction is carried out in a solvent such as methanol or N-methylpyrrolidinone at from 50° to 150° C and is complete in from 1–12 hours. Where the reaction temperature exceeds the reflux temperature of the reaction mixture, the reaction is carried out in a pressurized bomb. The product 2-methoxy compound is isolated using known techniques.

The compound wherein X is methylthio is prepared in a series of steps from the substituted 2-pyridone.

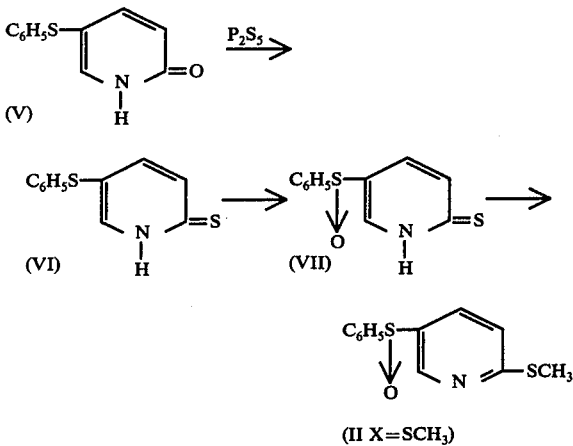

In the first step of the reaction sequence 5-phenylthio-2-pyridone (V) is treated with phosphorous pentasulfide to form the analogous pyridylthione (VI). In the reaction excess phosphorous pentasulfide is used and generally pyridine is used as a solvent. The reaction is heated at about 100° C for from 1 to 6 hours. The product is isolated using techniques known to those skilled in this art.

The 5-(phenylthio)-pyridine-2-thione (VI) is then oxidized to the sulfoxide (VII) using mild oxidizing agents. The preferred oxidizing agent is metachloroperbenzoic acid in a non-reactive solvent. The reaction is complete in from about 15 minutes to 2 hours and, in order to prevent oxidation of the thione group, the temperature is maintained at room temperature or less. The product is isolated using known techniques.

The 5-(phenylsulfinyl)-pyridine-2-thione (VII) is converted to the methylthio compound (II, X=SCH$_3$) by reacting it with dimethylsulfate. The reaction is carried out in basic solution in aqueous media. The bases employed are generally alkali metal hydroxides such as sodium or potassium hydroxide. The dimethylsulfate is generally used in excess quantities and the reaction is complete in from 1 to 3 hours at from room temperature to 50° C.

In any of the foregoing processes the phenylthio compound may be employed as the starting material, and the oxidation thereof deferred until the completion of the reaction sequence. The reaction conditions above described for the processes involving the phenylsulfinyl compound would be unchanged for the reaction involving the phenylthio compound. The compound thus produced would be the 2-methyoxycarbonylamino)-6-(phenylthio) imidazo [1,2-a] pyridine. This compound could be oxidized to the analogous phenylsulfinyl compound with mild oxidizing agents such as metachloroperbenzoic acid, peracetic acid or hydrogen peroxide. Non-reactive solvents are employed and the reaction is generally complete in from 2 to 10 hours at from room temperature to 50° C.

The compounds prepared by the processes of this invention are useful for the treatment and control of helminthiasis, a parasitic disease which causes widespread and often serious infections in domesticated animals such as cattle and sheep, and in man. The compounds are normally used in unit dosage forms such as tablets, capsules, drenches, paste formulations and the like, wherein the active ingredient is intimately admixed with a suitable inert carrier. The compound may also be employed in feeds.

EXAMPLE 1

5-(Phenylthio)-2-pyridone

A solution of 5-bromo-2-pyridone (17.3 g 0.1 mole) in N-methylpyrrolidinone (250 ml.) and potassium thiophenoxide (18.1 g, 0.12 mole) is heated at reflux for 12 hours under a nitrogen atmosphere. The reaction mixture is cooled and diluted with water. The product is collected by filtration, washed with water and dried to yeild 5-(phenylthio)-2-pyridone.

EXAMPLE 2

2-Chloro-5-(phenylthio)-pyridine

A suspension of 5-(phenylthio)-2-pyridone (4.06 g., .02 mole) in 50 ml. of phosphorous oxychloride containing 10 g. of phosphorous pentachloride is heated at reflux for 6 hours. Excess phosphorous oxychloride is removed in vacuo and the residue is poured onto icewater mixture. The mixture is cooled and the pH adjusted to neutral with dilute aqueous sodium hydroxide. The resultant suspension is extracted with methylene chloride. The combined extracts are washed with water, dried and evaporated in vacuo to yield 2-chloro-5-(phenylthio)pyridine.

Alternatively, 2-amino-5-(phenylthio) pyridine (30 g., 0.15 moles) is added portionwise to 30 ml. of concentrated hydrochloric acid at 0°. The resultant suspension is cooled to −15° C and 20.7 g. of sodium nitrite in 40 ml. of water is added dropwise while keeping the temperature at −15° to −10° C. After stirring for an additional hour at −5° C, an aqueous 30% sodium hydroxide solution is slowly added to pH7 while not allowing the temperature to exceed 0° C. The resultant mixture is extracted with methylene chloride and the combined extracts are washed with water, dried and evaporated in vacuo to yield 2-chloro-5-(phenylthio) pyridine.

EXAMPLE 3

2-Bromo-5(phenylthio)pyridine

2-Amino-5-(phenylthio)pyridine (16.9 g., 0.1 mole) is added to 40 ml. of 48% hydrobromic acid, cooled to 10° C in an ice bath. While maintaining a temperature of 0°, the resultant hydrobromide salt is treated with 37.5 g. of bromine dropwise. The temperature is reduced and maintained at −10° while 14.0 g. of sodium nitrite in 200 ml. of water is added dropwise. After 1 hour at 0° C, the pH of the reaction mixture is adjusted to pH7 with 30% aqueous sodium hydroxide. Following the same workup as for the 2-chloro ananlogue, there is obtained 2-bromo-5-(phenylthio) pyridine.

EXAMPLE 4

5-(Phenylthio)-pyridine-2-thione

A solution of 5-(phenylthio)-2-pyridone (4.06 g.) in 50 ml. of pyridine containing 5.0 g. of phosphorous pentasulfide is heated at 100° C for 6 hours. The cooled reaction mixture is diluted with water. The product collected by filtration, washed with water and dried to yield 5-(phenylthio)pyridine-2-thione.

EXAMPLE 5

5-(phenylsulfinyl)pyridine-2-thione

Following the procedure of Example 7 described below, 5-(phenylthio) pyridine-2-thione is converted to 5-(phenylsulfinyl)-pyridine-2-thione, with m-chloroperbenzoic acid.

EXAMPLE 6

2-(Methylthio)-5-(phenylsulfinyl)pyridine

A solution of 5-(phenylsulfinyl)pyridine-2-thione (2.21 g., .01 moles) in 25 ml. of 2.5N sodium hydroxide is treated with 1.6 g. of dimethyl sulfate. After stirring at room temperature for 3 hours, the reaction mixture is extracted with methylene chloride. The extracts are washed with water, dried and evaporated in vacuo to yield 2-(methylthio)-5-(phenylsulfinyl)pyridine.

EXAMPLE 7

2-Chloro-5(phenylsulfinyl)pyridine

A solution of 2-chloro-5-(phenylthio) pyridine (2.21 g., .01 moles) in 50 ml. of methylene chloride is treated with a methylene chloride solution of 2.02 g. of 85% m-chloroperbenzoic acid. The solution is stirred at room temperature for 1 hour and washed with 50 ml. of aqueous saturated sodium bicarbonate solution. The organic layer is separated dried and evaporated in vacuo to yield 2-chloro-5-(phenylsulfinyl)pyridine.

EXAMPLE 8

2-Bromo-5-pheylsulfinylpyridine

Following the procedure of Example 7 2-bromo-5phenylthiopyridine is converted to 2-bromo-5-(phenylsulfinlyl) pyridine with m-chloroperbenzoic acid.

EXAMPLE 9

2(Methoxy-5-phenylthiopyridine

A solution of 2-bromo-5-phenylsulfinylpyridine (2.82 g., 0.01 mole) and 0.50 g. of sodium methoxide is heated in 50 ml. of refluxing methanol for 5 hours. The reaction mixture is evaporated in vacuo, and the residue is diluted with water. The solids are collected by filtration, washed with water and dried to yield 2-methoxy-5-phenylsulfinylpyridine.

EXAMPLE 10

2-Methoxy-5-phenylsulfinylpyridine

Following the procedure of Example 7 2-methoxy-5-phenylthio pyridine is converted to 2-methoxy-5-phenylsulfinyl pyridine with m-chloroperbenzoic acid.

EXAMPLE 11

2-(Methoxycarbonylamino)-6-(phenylsulfinyl)imidazo [1,2-a]pyridine

A solution of 2-chloro-5-(phenylsulfinyl)pyridine (2.37 g., .01 mole) in 10 ml. of hexamethylphosphoramide is treated with 2.2 g. of methylchloroacetylcarbamate. The solution is warmed to 50° C for 1 hour, cooled, combined with 5 ml. of methanol and saturated with anhydrous ammonia. The mixture is warmed at 100° C for 3 hours. After cooling, the reaction mixture is diluted with 5 volumes of ether and the crude product is collected by filtration. Recrystallization from hot methanol yields 2-(methoxycarbonylamino)-5-(phenylsulfinyl) imidazo [1,2-a] pyridine, m.p. 249°–251° C.

EXAMPLE 12

2(Methoxycarbonylamino)-6-(phenylsulfinyl)imidazo [1,2-a]pyridine

The procedure of Example 11 may be repeated using 2-bromo-5-(phenylsulfinyl)pyridine, 2methoxy-5-(phenylsulfinyl)pyridine, or 2-(methylthio)-5(phenylsulfinyl) pyridine as starting materials. The product produced is 2-(methoxycarbonylamino)-6-(phenylsulfinyl)-imidazo [1,2-a] pyridine.

EXAMPLE 13

2(Methoxycarbonylamino)-6-(phenylthio)imidazo [1,2-a]pyridine

The procedure of Example 11 may be repeated using 2-chloro-5-(phenylthio)pyridine as the starting material affording as product 2-(methoxycarbonylamino)-6-(phenylthio)imidazo [1,2-a] pyridine.

EXAMPLE 14

2-(Methoxycarbonylamino)-6-(phenylsulfinyl)imidazo [1,2-a]pyridine

10 G. of 2-(methoxycarbonylamino)-6-(phenylthio) imidazo [1,2-a] pyridine is suspended in 200 ml. of acetic acid, treated with 40 ml. of 30% hydrogen peroxide and stirred at room temperature for 4 hours. The reaction mixture is filtered and the filtrate combined with 600 ml. of water and stirred at room temperature for 15 minutes. The mixture is filtered and the solid material is dissolved in 175 ml. of dimethyl formamide at 80° C, filtered and the filtrate is diluted with 175 ml. of ethanol. Upon cooling, the solids are collected by filtration and washed 3 times with ether affording 2-(methoxycarbonylamino)-6-(phenylsulfinyl) imidazo [1,2-] pyridine, m.p. 249-251° C.

What is claimed is:

1. A process for the preparation of a compound having the formula:

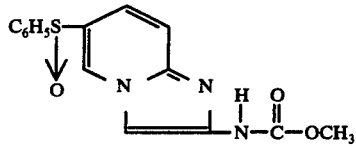

which comprises treating a compound having the formula:

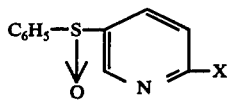

wherein X is a halogen, loweralkoxy or loweralkylthio, with methyl chloroacetyl carbamate to form:

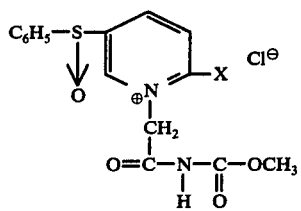

which is treated with ammonia and then heated in order to form the desired product.

2. The process of claim 1 wherein X is chlorine, bromine, methoxy or methylthio.

3. The process of claim 2 wherein the heating step is carried out in the presence of methanol.

4. A process for the preparation of a compound having the formula:

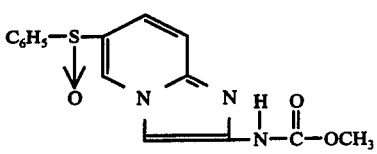

which comprises treating a compound having the formula:

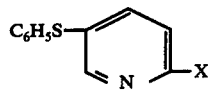

wherein X is a halogen, loweralkoxy or loweralkylthio, with methylchloroacetylcarbamate to form:

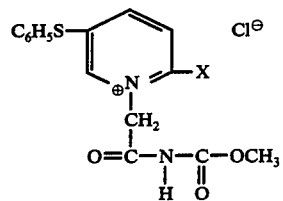

which is treated with ammonia and then heated in order to form:

$$C_6H_5S\text{—pyridine-imidazo—NH—C(O)—OCH}_3$$

which is oxidized to the desired product.

5. The process of claim 4 wherein X is chlorine, bromine, methoxy or methylthio.

6. The process of claim 5 wherein the heating step is carried out in the presence of methanol.

* * * * *